United States Patent [19]

Weiershausen et al.

[11] Patent Number: 4,861,770
[45] Date of Patent: Aug. 29, 1989

[54] USE OF BENZOTHIAZEPINE DERIVATIVES AS LYMPHOCYTE PROTECTORS

[75] Inventors: Ute Weiershausen, Gundelfingen; Volker Ganser, Freiburg; Gerhard Satzinger, Denzlingen, all of Fed. Rep. of Germany

[73] Assignee: Goedecke Aktiengesellschaft, Berlin, Fed. Rep. of Germany

[21] Appl. No.: 150,578

[22] Filed: Feb. 1, 1988

[30] Foreign Application Priority Data

Feb. 18, 1987 [DE] Fed. Rep. of Germany ....... 3705117

[51] Int. Cl.$^4$ ............................................. A61K 31/55
[52] U.S. Cl. .................................................. 514/211
[58] Field of Search ........................................ 514/211

[56] References Cited

U.S. PATENT DOCUMENTS

| | | | |
|---|---|---|---|
| 4,628,047 | 12/1986 | Sakurai et al. | 514/211 |
| 4,663,317 | 5/1987 | Albrecht et al. | 514/211 |
| 4,690,935 | 9/1987 | Taylor et al. | 514/211 |

*Primary Examiner*—Jerome D. Goldberg
*Attorney, Agent, or Firm*—Elizabeth M. Anderson

[57] ABSTRACT

The use of benzothiazepine derivatives for the protection of lymphocytes in humans and higher mammals, especially in the treatment of acquired immune deficiency syndrome.

1 Claim, 3 Drawing Sheets

USE OF BENZOTHIAZEPINE DERIVATIVES AS LYMPHOCYTE PROTECTORS

BACKGROUND OF THE INVENTION

The present invention is concerned with the use of benzothiazepine derivatives, especially diltiazem, for the protection of lymphocytes.

Acquired immune deficiency syndrome (AIDS) is a very serious infectious disease against which hitherto no effective agents have been found.

Germany Patent No. 1805714 covers benzothiazepines, with tranquilizer effect which is said to be superior to that of chlordiazepoxide. It was later found that the there-described compounds had, at least in part, a calcium antagonistic effect. One,2-(4-methoxyphenyl)-3-acetoxy-5-($\beta$-dimethylaminoethyl)-2,3-dihydro-1,5-benzo- thiazepin-4(5H)-one (diltiazem), especially the hydrochloride thereof, is a well known calcium antagonist and is used worldwide.

A further highly interesting indication can be attributed to the class of compounds known from German Patent No. 1805714, namely, a surprising protective action with respect to immune-competent lymphocytes.

SUMMARY OF THE INVENTION

The present invention is concerned with the use of benzothiazepine derivatives of the formula

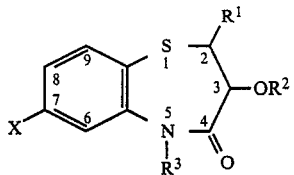

wherein $R^1$ is a hydrogen atom or a phenyl radical which is optionally substituted by a methyl radical, one to three methoxy radicals or one to two chlorine atoms, $R^2$ is a hydrogen atom or an acetyl radical, X is a hydrogen or chlorine atom, and $R^3$ is a hydrogen atom or a radical of the formula

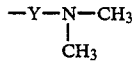

wherein Y is an alkylene radical with two or three carbon atoms, and of the pharmaceutically useful salts thereof for the protection of lymphocytes of humans and of higher mammals.

The use of diltiazem hydrochloride is especially preferred.

DETAILED DESCRIPTION OF THE INVENTION

Figure 1:
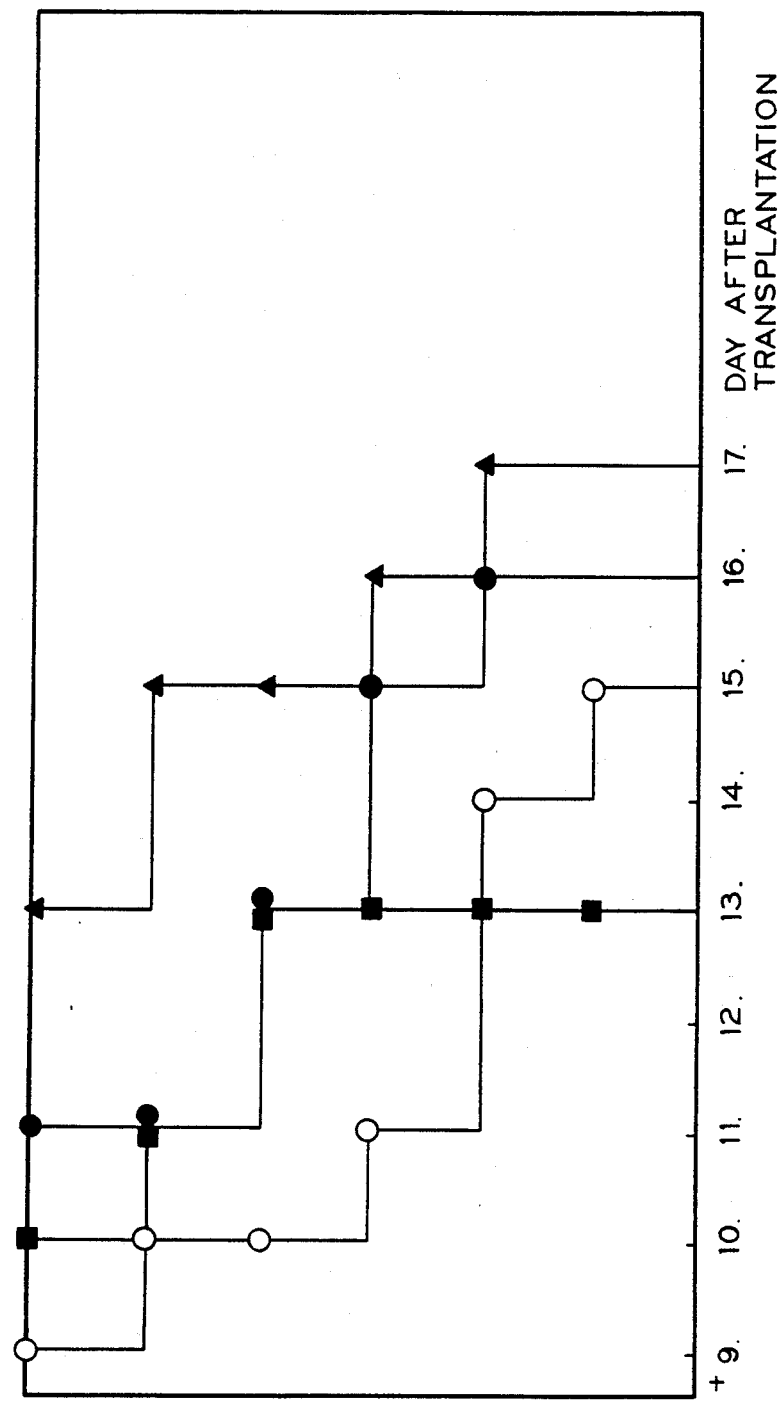
FIG. 1 shows the skin-allograft-survival (days) of rats after oral application of dinalin and diltiazem and combinations thereof compared to control.
 o is the control.
 ▲ is dinalin at 10 mg/kg/day, −3 to +2.
  5 mg/kg/day +3 to +6.
 ● is dinalin at 10 mg/kg/day, −to 2.
  5 mg/kg/day +3 to +6.
  is diltiazem at 200 mg/kg/day −3 to 30 6.
 ■ is diltiazem at 200 mg/kg/day −3 to +6.

The compounds of Formula I above are agents with the help of which toxic actions on lymphocytes caused by medicaments or by lymphocytotropic viruses can be prevented. They make possible a new therapeutic concept in the sense of a "selective lymphocyte protection".

Lymphocytotoxic medicaments, understood to be different classes of active materials, for example cytostatics, antibiotics and antihypertensives, insofar as these either reduce the number of lymphocytes circulating in the blood or impair their immunological functions. Both effects lead to a more or less marked failure of the immune defense with the result of a higher infection susceptibility of the organism. In the case of cytostatics, in particular, lymphocytopoietic-acting cytostatics, such as cyclophosphamide, because of a cell proliferation-inhibiting activity, most cases result in an accumulation of immature and immune-incompetent lymphocyte precursors in the bone marrow. At the same time the number of mature and immunologically functionable lymphocytes circulating in the blood decreases.

The second type of action results, in the case of unchanged lymphocyte count, in a change of the lymphocyte functions. This effect can come about in different ways. For example, the immune suppressive cyclosporin A inhibits the activation of the actual defense lymphocytes (cytotoxic T-lymphocytes) via an inhibition of the production of the activating messenger material by the so-called T-helper lymphocytes. Furthermore, in the case of this substance, there has also been discussed an inhibition of the formation of those receptors on cytotoxic T-cells to which the messenger substances activating them bind.

Also by reversible blocking of these receptors by noncytotoxic substances, there is achieved a protection of the lymphocyte surface against lymphocytotropic noxae.

By lymphocytrophic noxae, in the present case there are also to be understood lymphocytotropic viruses. As is known, the actual infection of the cells by these pathogens is first preceded by the binding thereof to certain receptors on the cell surface, whereafter the receptor-virus complex then invaginates into the interior of the cell. Lymphocytotropic viruses can either transform their target cell malignantly, or provoke their elimination by virus-induced autoimmune processes (HIV in the case of T-helper cells). Hitherto, there has been no known effective medication for the above-mentioned lymphocytotropic virus infections. In general, because of the virus-induced massive immune insufficiency, the patient succumbs to generalized infections.

Consequently, the special problem of the lymphocytotropic viruses in comparison with the nonlymphocytotropic viruses is that they preferentially infect cells of the immune system and, therefore, exclude precisely those mechanisms which are essential for the elimination of these viruses themselves, as well as also accompanying opportunistic pathogens.

It is the object of the present invention to provide noncytotoxic substances which are characterized by a generally high compatibility, which displace binding partners of a chemical or viral nature which are toxic for lymphocytes from their specific receptors on the lymphocyte surfaces or which prevent their interaction with these target cells via other mechanisms.

In the case of lymphocytotoxic cytostatics, the immune suppression which limits the dosage in the case of these antitumor agents and which frequently endanger the life of the patients can be prevented. Furthermore, over a long period of time, it is also possible to influence the known induction of secondary tumors by cytostatics, the formation of which is favored by the iatrogenic immune weakness.

In the case of lymphocytotropic viruses, according to the present invention, the receptors used by pathogens for attachment to lymphocyte surfaces can be blocked in a nontoxic way. Here there is a prophylaxis in risk situations and also, in the case of already manifest infection, the prevention of the infection by further immune cells subsequently provided by the bone marrow. A restitution of the immune competence is to be expected. This has not been possible in the case of HIV infections (AIDS infections), for example, for achieving a maintenance of the life of the patient.

In experiments for the antagonization of the immune-suppressive action of the antineoplastic substance, dinalin, (r-amino-N-(2'-aminophenyl)-benzamide; (European Patent Application 116,967), in a skin transplant model in rats it was demonstrated for the first time that diltiazem in a dosage of 200 mg/kg/day, administered intragastrally, clearly antagonized the immune-suppressive activity of dinalin (see Table I and FIG. 1 below). Since the immunesuppressive activity in this model comes about via an inhibition of cytotoxic T-lymphocytes or of the functions thereof, there can be deduced a protection of this cell population by diltiazem against the antiproliferative action of this antineoplastic. That diltiazem must have an influence on cytotoxic T-lymphocytes was also made clear in that the substance, administered alone, itself brought about a moderate reduction of the transplantation rejection (see Table 1 below).

Via the low density lipoproteins (LDL) receptors, the cholesterol-rich lipid components of the serum are introduced into the cells. The increased occurrence of these receptors on lymphocyte surfaces is possibly to be regarded in conjunction with their higher rate of division which brings with it an increased consumption of the membrane constructional component cholesterol. The known binding of diltiazem to the LDL receptors can be responsible for its membrane action or displacement mechanisms also towards viral binding components on lymphocyte surfaces. The increased LDL receptor density on lymphocytes could also explain the selectivity of the demonstrated protective action for the lymphocyte population.

The reversible, noncytotoxic arresting of the lymphocyte proliferation and the influencing of receptors on the lymphocyte surfaces can, consequently, represent mechanisms of the lymphocyte protection according to the present invention towards chemical and virally-caused lymphocytotropic noxae by the compounds of Formula I.

Experiments for the protection of T-lymphocytes against medicament-induced lymphocytotoxic effects were carried out on a rat skin transplant model according to Waynforth (Experimental and Surgical Techniques in the Rat, Academic Press, 1980), modified according to Heystek. Two allogenic skin transplants were, in each case, transferred from histoincompatible donor rats to recipient rats. The transplants were obtained with a punch, freed preparatively from panniculus carnosus and placed into transplant beds of the recipient, which were also punched out. The transplants were covered with a special dressing material and fixed with a bandage. The end point of the investigation was the day on which at least 50% of the animals have rejected both transplants. The immune-suppressive activity of an active material is determined on the basis of the prolongation of the normal transplant survival in days of the untreated control animals (FIG. 1, Table 1).

Furthermore, experiments were carried out for the influencing of the cyclophosphamide-induced lymphopenia in rats. One group, which exclusively received diltiazem, served as control. Two dosages of cyclophosphamide, administered as individual doses, were compared with a combination of the cytostatic with diltiazem, the combination treatment being preceded by a two-day pretreatment with diltiazem. The determination of the leukocyte and lymphocyte counts took place in blood which, in each case, had been taken on the morning before the administration of substance from the retro-orbital cavity under short-term penthranenarcosis. The results obtained are set out in FIGS. 2 and 3 of the accompanying drawings.

The demonstration of the lymphocyte protection against lymphocytotropic viruses was carried out in vitro on the basis of treated human lymphocytes or lymphocyte cell lines in culture and $^{125}$-labeled, heat-inactivated HIV. After incubation of the cells with the virus, the radioactivity was determined in comparison with untreated control lymphocytes, using a Geiger counter. Diphenylhydantoin was used as positive standard (Dtsch. Med. Wochensch., 25, 1001–1002/1986).

Figure 2:
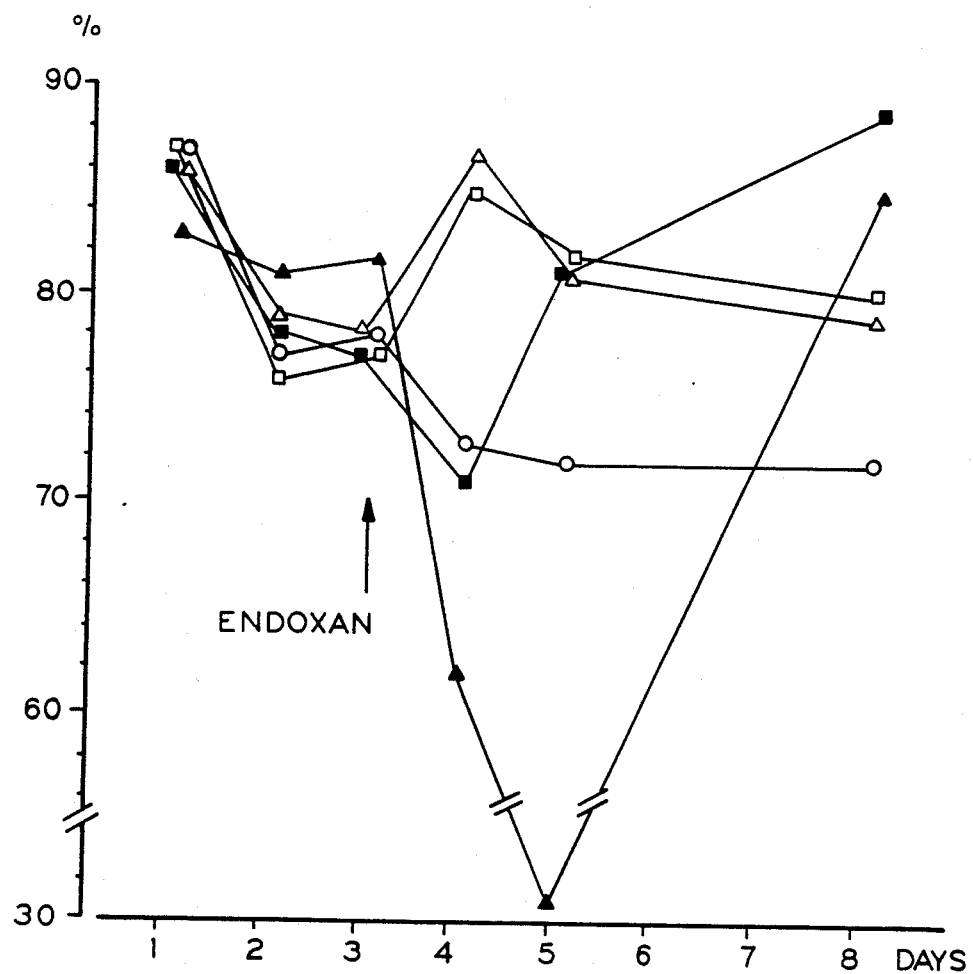
FIG. 2 shows lymphocytes in % of total leukocytes.
 o is diltiazem at 200 mg/kg i.g. (control)
 Δ is 50 at mg/kg i.g.} Methocel +
 ▲ is 150 at mg/kg i.g.} Endoxan
 □ is 150 at mg/kg i.g.} Diltizem +
 ■ is 150 mg/kg i.g.} Endoxan
Figure 3:
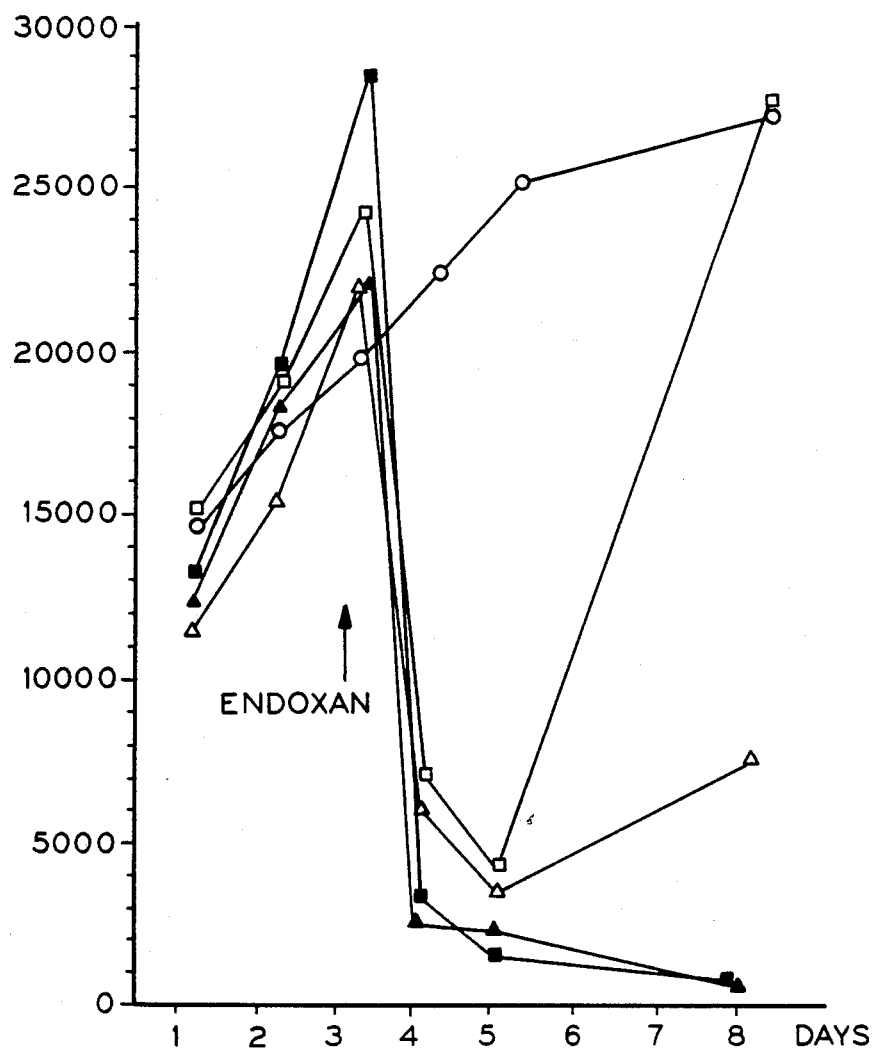
FIG. 3 shows the leukocyte count of SD-rats.
 o is diltiazem at 200 mg/kg i.g. (control)
 Δ is 50 at mg/kg i.g.} Methocel
 ▲ is 150 at mg/kg i.g.} Endoxan
 is □ 50 at mg/kg i.g.} Diltiazem +
 ■ is 150 at mg/kg i.g.} Endoxan

Using the example of the strongly leukopoenically-acting cytostatic cyclophosphamide, it was shown that an intragastral pretreatment with diltiazem in a dosage of 200 mg/kg/day completely prevented the massive lymphocytopenia induced by high oral single doses of 150 mg/kg cyclophosphamide in rats (FIG. 2). The granulocytopoenia also induced by cyclophosphamide was not influenced by diltiazem (FIG. 3). Consequently, it is an effect which is specific for lymphocytes.

Furthermore, it was investigated whether diltiazem influences the immune-suppressive activity of such substances in which this comes about not via lymphopoenic actions but via inhibition of lymphocyte functions. Cefradin is not lymphocytopenic but has a strongly immunesuppressive action. A simultaneous treatment of the animals with diltiazem leads, in the case of this substance at higher dosages, to a substantial removal of this activity (see Table 1). In the case of the combination treatment, diltiazem was, in each case, administered before the substance to be antagonized, namely, at an interval of at least half an hour.

On the basis of all of the experiments carried out, it is obvious that the compounds of Formula I, especially diltiazem, in appropriate dosage, make possible a selective protection of peripheral lymphocytes, especially of T-lymphocytes, against quantitative and qualitative damage of this cell population caused by medicaments. In particular, on the basis of the antagonizing of the immune-suppressive action of cefradin, which takes place on the receptor plane, this also includes the protection against viral lymphocytotropic binding components, for example HIV, in the activity spectrum of the substances according to the present invention.

In the case of orientating experiments with the compounds of Formula I, it has been found that these, via a direct membrane action, change the binding places of the cells for the AIDS virus so that it can be assumed that, for example, diltiazem is suitable for combatting AIDS in humans within the compatible dosage range of from 10 to 100 mg per orally administered individual dose.

The compounds of Formula I can, according to the present invention, be administered to humans enterally or parenterally in liquid or solid form. As injection medium, it is especially preferred to use aqueous media which contain conventional additives, such as stabilizing agents and solubilizing agents. Solid carrier materials include, for example, starch, lactose, mannitol, methyl cellulose, talc, highly dispersed silicic acids, high molecular weight fatty acids (such as stearic acid), gelatin, agar-agar, calcium phosphate, magnesium stearate, animal and vegetable fats, and solid high molecular weight polymers (such as polyethylene glycols). Compositions suitable for oral administration can, if desired, contain flavoring and/or sweetening agents.

Besides diltiazem, according to the present invention the following compounds, all of which are covered in German Patent No. 1805714 can be used:

2-(4-chlorophenyl)-3-hydroxy-5-β-dimethylaminoethyl)-2,3-dihydro-1,5-benzothiazepin-4(5H)-one;

2-(3,4,5-trimethoxyphenyl)-3-hydroxy-5-(β-dimethylaminoethyl)-7-chloro-2,3-dihydro-1,5-benzothiazepin-4-(5H)-one perchlorate;

2-(4-methylphenyl)-3-hydroxy-5-(β-dimethylaminoethyl)-7-chloro-2,3-dihydro-1,5-benzothiazepin-4(5H)-one hydrochloride;

2-(2,4-dichlorophenyl)-3-hydroxy-5-(β-dimethylaminoethyl)-7-chloro-2,3-dihydro-1,5-benzothiazepin-4-(5H)-one hydrochloride;

2-(4-methylphenyl)-3-hydroxy-5(β-dimethylaminoethyl)-2,3-dihydro-1,5-benzothiazepin-4(5H)-one;

2-4-methoxyphenyl)-3-hydroxy-5-(β-dimethylaminoethyl)-7-chloro-2,3-dihydro-1,5-benzothiazepin-4(5H)-one;

2-(4-chlorophenyl)-3-hydroxy-5-(β-dimethylaminoethyl)-7-chloro-2,3-dihydro-1,5-benzothiazepin-4(5H)-one hydrochloride;

2-phenyl-3-hydroxy-5-(β-dimethylaminoethyl)-2,3-dihydro-1 -one;

2-(3,4-dimethoxyphenyl)-3-hydroxy-5-(β-dimethylaminoethyl)-2,3-dihydro-1,5-benzothiazepin-4(5H)-one hydrochloride;

2-(3,4,5-trimethoxyphenyl)-3-hydroxy-5-(β-dimethylaminoethyl)-2,3-dihydro-1,5-benzothiazepin-4(5H)-one hydrobromide;

2-(2,4-dichlorophenyl)-3-hydroxy-5-(β-dimethylaminoethyl)-2,3-dihydro-1,5-benzothiazepin-4(5H)-one hydrochloride; 2-(3,4-dimethoxyphenyl-3-hydroxy-5-(β-dimethylaminoethyl)-7-chloro-2,3-dihydro-1,5-benzothiazepine-4(5)-one hydrochloride;

2-(4-methoxyphenyl)-3-hydroxy-5-(β-dimethylaminoethyl)-2,3-dihydro-1,5-benzothiazepin-4(5H)-one;

2-phenyl-3-hydroxy-5-(γ-dimethylamino-n-propyl)2,3-dihydro-1,5-benzothiazepin-4(5H)-one;

2-(4-methoxyphenyl)-3-hydroxy-5-(γ-dimethylamino-n-propyl)-2,3-dihydro-1,5-benzothiazepin-4(5H)-one hydrochloride;

2-(3,4,5-trimethoxyphenyl)-3-hydroxy-5-(γ-dimethylamino-n-propyl)-2,3-dihydro-1,5-benzothiazepin-4(5H)-one hydrochloride;

2-(4-methylphenyl)-3-hydroxy-5-(γ-dimethylamino-n-propyl)-2,3-dihydro-1,5-benzothiazepin-4(5H)-one hydrochloride;

2-phenyl-3-hydroxy-5-(γ-dimethylamino-n-propyl)-7-chloro-2,3-dihydro-1,5-benzothiazepin-4(5H)-one oxalate;

2-(4-chlorophenyl)-3-hydroxy-5-(γ-dimethylamino-n-propyl)-7-chloro-2,3-dihydro-1,5-benzothiazepin-4(5H)-one hydrochloride;

2-(4-methoxyphenyl)-3-hydroxy-5-(α-methyl-β-dimethylaminoethyl)-2,3-dihydro-1,5-benzothiazepin-4(5H)-one oxalate;

2-(4-methoxyphenyl)-3-hydroxy-5-(γ-dimethylamino- n-propyl)-7-chloro-2,3-dihydro-1,5-benzothiazepin-4(5H)-one;

2-phenyl-3-acetoxy-5-(β-dimethylminoethyl)-2,3-dihydro-1,5-benzothiazepin-4(5H)-one; 2-(4-methoxyphenyl)-3-acetoxy-5-(β-dimethylaminoethyl)-2,3-dihydro-1,5-benzothiazepin-4(5H)-one hydrochloride;

2-(3,4,5-trimethoxyphenyl)-3-acetoxy-5-(β-dimethylaminoethyl)-2,3-dihydro-1,5-benzothiazepin-4(5H)-one oxalate;

2-(4-methylphenyl)-3-acetoxy-5-(β-dimethylaminoethyl)-2,3-dihydro-1,5-benzothiazepin-4(5H)-one hydrochloride;

4-phenyl-3-acetoxy-5-(β-dimethylaminoethyl)-7-chloro-2,3-dihydro-1,5-benzothiazepin-4-(5H)-one hydrochloride;

2-(4-methoxyphenyl)-3-acetoxy5-(β-dimethylaminoethyl)-7-chloro-2,3-dihydro-1,5-benzothiazepin-4(5H)-one hydrochloride;

2-(4-chlorophenyl)-3-acetoxy-5-(β-dimethylaminoethyl)-7-chloro-2,3-dihydro-1,5-benzothiazepin-4(5H)-one hydrochloride;

2-phenyl-3-acetoxy-5-(γ-dimethylamino-n-propyl)-2,3-dihydro-1,5-benzothiazepin-4(5H)-one hydrochloride;

2-(4-methylphenyl)-3-acetoxy-5-(γ-dimethylamino-n-propyl)-2,3-dihydro-1,5-benzothiazepin-4(5)-one hydrochloride;

2-(3,4,5-trimethoxyphenyl)-3-acetoxy-5-(γ-dimethylamino-n-propyl)-2,3-dihydro-1,5-benzothiazepin-4(5H)-one hydrochloride;

2-phenyl-3-acetoxy-5-(γ-dimethylamino-n-propyl)-7-chloro-2,3-dihydro-1,5-benzothiazepin-4(5H)-one hydrochloride;

2-(4-methoxyphenyl)-3-acetoxy-5-(γ-dimethylamino-n-propyl)-7-chloro-2,3-dihydro-1,5-benzothiazepin-4(5H)-one hydrochloride; or 2-(4-chlorophenyl)-3-acetoxy-5-(γ-dimethylamino-n-propyl)-7-chloro-2,3-dihydro-1,5-benzothiazepin-4(5H)-one hydrochloride.

TABLE 1

Influence of Diltiazem on the Activity of a Lympocytopenic (Dinalin) and of a Nonlymphocytopenic (Cefradin**) Immune Suppressive Model: skin transplant survival test; rats.
recipient: Long Evans male; donor Lewis male.
The day is determined on which at least 50% of the animals of a group have rejected both transplants

| Test Substance, Dosage | Animals With 2 Rejected Transplants/n (%) | | | | | | | | |
|---|---|---|---|---|---|---|---|---|---|
| | Day +9 | 10 | 11 | 12 | 13 | 14 | 15 | 16 | 17 |
| Control Methocel i.g. | 1/8 (17) | 3/6 (50) | 4/6 (66) | 4/6 (66) | 4/6 (66) | 5/6 (83) | 6/6 (100) | | |
| Dinalin 10 mg/kg i.g. day −3−+2 5 mg/kg i.g. day +3−+6 | 0/5* (0) | 0/5 (0) | 0/5 (0) | 0/5 (0) | 1/5 (20) | 1/5 (20) | 3/5 (60) | 4/5 (80) | 5/5 (100) |
| Diltiazem 200 mg/kg i.g. day −3−+6 | 0/6 (0) | 1/6 (17) | 2/6 (33) | 2/6 (33) | 6/6 (100) | | | | |
| Dinalin 10 mg/kg i.g. day −3−+2 5 mg/kg i.g. day +3−+6 and Diltiazem 200 mg/kg i.g. day −3−+6 | 0/5* (0) | 0/5 (0) | 2/5 (40) | 2/5 (40) | 3/5 (60) | 3/5 (60) | 4/5 (80) | 5/5 (100) | |
| Cefradin 1000 mg/kg i.g. day −3−+6 and Diltiazem 200 mg/kg i.g. day −3−+6 | 0/6 (0) | 1/6 (17) | 3/6 (50) | 5/5* (100) | | | | | |

*Animal died in the course of the experiment
**Cefradin = 7-[D-2-amino-2-(1,4-cyclohexadien-1-yl)-acetamido]-3-methyl-8-oxo-5-thia-1-azabicyclo[4,2,0]-oct-2-ene-2-carboxylic acid (Rote Liste, 1987, No. 10.084)

We claim:

1. A method for treating lymphocytotropic virus in human or higher mammals which comprises administering to said human or higher mammal in need thereof from 10 to 100 mg per orally administered dose of a compound of

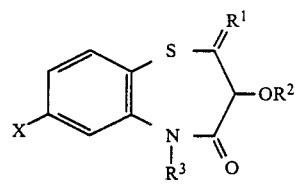

or a pharmaceutically acceptable salt thereof, wherein
$R^1$ is hydrogen, phenyl, phenyl substituted by methyl, one to three methoxy groups, or one to two chlorine atoms,
$R^2$ is hydrogen or acetyl,
X is hydrogen or chlorine, and
$R^3$ is hydrogen or a group of formula

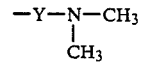

wherein Y is alkylene of from two to three carbon atoms.

* * * * *